United States Patent [19]

Mukaiyama et al.

[11] 4,105,673

[45] Aug. 8, 1978

[54] PROCESS FOR THE PREPARATION OF LACTONES

[75] Inventors: Teruaki Mukaiyama; Masahiro Usui, both of Tokyo; Kazuhiko Saigo, Chiba, all of Japan

[73] Assignee: Sumitomo Chemical Company, Limited, Osaka, Japan

[21] Appl. No.: 724,845

[22] Filed: Sep. 20, 1976

[30] Foreign Application Priority Data

Jan. 13, 1976 [JP] Japan ..................... 51-3557

[51] Int. Cl.$^2$ ........................... C07D 313/00
[52] U.S. Cl. ..................................... 260/343
[58] Field of Search ........................ 260/343

[56] References Cited

PUBLICATIONS

Corey et al., J. Amer. Chem. Soc., 96, p. 5614, 1974.
Osamu Okuda, Perfume Chemical Index, pp. 1209–1216, 1968.
Poucher et al., Perfumes, Cosmetics and Soaps, vol. 1, pp. 29 and 163–164, published in 1974.
Apsimon, "The Total Syn. of Natural Products", vol. 1, pp. 426–433, Wiley, 1973.
J.A.C.S., vol. 78, 6390–6393, 1956.
Hel. Chi. Acta., vol. 46, pp. 1235–1243, 1963.

*Primary Examiner*—Natalie Trousof
*Assistant Examiner*—Jane T. Fan
*Attorney, Agent, or Firm*—Stevens, Davis, Miller & Mosher

[57] ABSTRACT

An improved process for producing a large ring lactone which comprises subjecting a hydroxy acid to intramolecular condensation by the use of a 1-substituted-2-halopyridinium salt or a 1-substituted-2-haloquinolinium salt as a condensing agent in the presence of an acid captor in an anhydrous organic solvent. According to this process, a variety of lactones, even complex lactones such as macrolides can be obtained in good yields.

6 Claims, No Drawings

PROCESS FOR THE PREPARATION OF LACTONES

The present invention relates to a novel process for producing large ring lactones. More particularly, the invention pertains to an improved process for producing large ring lactones which comprises subjecting a hydroxy acid to intramolecular condensation by the use of a 1-substituted-2-halopyridinium salt or a 1-substituted-2-haloquinolinium salt as a condensing agent in the presence of an acid captor for acids having an anion selected from the group consisting of halogen, methylsulfate, p-toluenesulfonate, perchlorate and tetrafluoroborate captor in an anhydrous organic solvent.

There are various structures of large ring lactones, some of which are known to have a useful biological activity like those which are known as macrolides.

So far, there have been reported several synthetic processes for the preparation of such large ring lactones. It is, however, difficult or sometimes impractical to apply these known processes to the preparation of a large ring lactone having a complicated structure because of severe reaction conditions or low yields. For example, large ring lactones may be prepared by lactonization of a hydroxy acid with trifluoroacetic anhydride or phosgene, but this process produces the desired lactones only in very low yields when applied to the preparation of lactones having an 8 or more membered ring.

An improved process for the lactonization of hydroxy acids has been reported in J. Amer. Chem. Soc., 96, 5614 (1974) and 97, 3515 (1975); but applicability of this process is somewhat limited because it requires the use of a heavy metal, a high reaction temperature and a long reaction time.

As the result of an intensive study, it has now been found that by the use of a 1-substituted-2-halopyridinium salt or a 1-substituted-2-haloquinolinium salt as a condensing agent in the presence of an acid captor for acids having an anion selected from the group consisting of halogen, methylsulfate, p-toluenesulfonate, perchlorate and tetrafluoroborate lactonization of a hydroxy acid can be carried out under mild reaction conditions and in very high yields. According to this process, various lactones, even those having a complicated structure such as natural products, can be prepared.

Thus, the process of the present invention can be used advantageously for the preparation of large ring lactone having a complicated structure, such as macrolides, which have several asymmetric atoms and which were hitherto too difficult to synthesize.

The 1-substituted-2-halopyridinium salts used in the present invention can be represented by the formula:

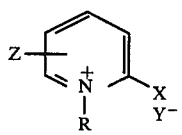

wherein R is $C_1$–$C_6$ alkyl, allyl, $C_3$–$C_6$ cycloalkyl-($C_1$–$C_2$)alkyl, 2-oxo-($C_2$–$C_6$)alkyl, phenyl-($C_1$–$C_6$) alkyl or phenyl-substituted 2-ox0-($C_2$–$C_6$) alkyl; X is halogen; $Y^-$ is a halide ion, a methylsulfate ion, a p-toluenesulfonate ion, a perchlorate ion or a tetrafluoroborate ion; and Z is $C_1$–$C_6$ alkyl, nitro, halogen or $C_1$–$C_6$ alkoxy.

The 1-substituted-2-haloquinolinium salts can be represented by the formula:

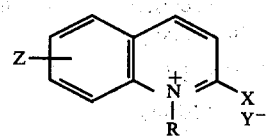

wherein R, X, $Y^-$ and Z are as defined above.

Among the 1-substituted-2-halopyridinium salts and the 1-substituted-2-haloquinolinium salts, the following are particularly preferred: 2-Chloro-1-methylpyridinium iodide, 2-iodo-1-methylpyridinium methyl sulfate, 2-chloro-1-ethylpyridinium bromide, 1-benzyl-2-chloropyridinium bromide, 2-chloro-1-phenacylpyridinium chloride, 2-fluoro-1-methylpyridinium p-toluenesulfonate, 2-bromo-1-methylpyridinium perchlorate, 1-ethyl-2-iodoquinolinium iodide, 2-chloro-1-ethyl-4-methoxypyridinium tetrafluoroborate and 2,6-dichloro-1-ethylpyridinium tetrafluoroborate.

The acid captors used in the process of the present invention may be tertiary amines of the formula:

$$R_1R_2R_3N$$

wherein $R_1$, $R_2$ and $R_3$ each are $C_1$–$C_{15}$ alkyl, allyl or $C_3$–$C_6$ cycloalkyl-($C_1$–$C_2$) alkyl; or betaines which, in the present specification, refers to compounds having an anion and a cation in their molecule.

Typical examples of said tertiary amines are triethylamine, tri-n-butylamine, N,N-dimethylbutylamine, N,N-dimethylcyclohexylamine, lutidine, collidine, N-methylpyrrolidine, N-methylmorpholine, 1,5-diazabicyclo-[4,3,0]nonene-5, 1,4-diazabicyclo[2,2,2]octane and 1,5-diazabicyclo[5,4,0]undecene-5.

Examples of preferred betaines are 3,4-dihydro-2H-pyrido[1,2-a]pyrimidin-2-one, triethylammonium acetate, 1-oxonianaphthalene-7-carboxylate and (1-methyl-4-pyridinio) acetate.

In carrying out the process of the present invention, the amount of 1-substituted-2-halopyridinium salt or 1-substituted-2-haloquinolinium salt used is not particularly limited; but good results can be obtained when these salts are used in a molar ratio of one to five times the the amount of hydroxy acid. The molar ratio of the acid captor to the 1-substituted-2-halopyridinium salt or 1-substituted-2-haloquinolinium salt in the reaction mixture is also not particularly limited; but the preferred ratio is 2:1.

The process of this invention can be carried out in the presence of an anhydrous organic solvent. Preferred examples of such solvents are ethyl ether, toluene, tetrahydrofuran, benzene, xylene, acetonitrile, 1,2-dimethoxyethane, methylene dichloride, chloroform or carbon tetrachloride. The reaction can be carried out at a temperature of 0° C to the boiling point of the solvent used; but the latter temperature is preferable.

The lactonization process of this invention can be applied to various types of hydroxy acids having a hydroxy group in the γ; or more remote position in their chain. The hydroxy acids may be substituted by a variety of substituents, as for example, alkyl, vinyl, cycloalkyl, etc.

Examples of such hydroxy acids are 6-hydroxyhexanoic acid, 8-hydroxyoctanoic acid, 8-hydroxydecanoic acid, 10-hydroxydecanoic acid, 11-hydroxytetradencanoic acid, 16-hydroxy-7-hexadecenoic acid and 12-hydroxy-9,15-octadecadienoic acid.

The following specific examples are presented to illustrate the invention more precisely but they should not be construed to limit the scope thereof.

EXAMPLE 1

To a refluxing solution of 510 mg (2.0 mmol) of 2-chloro-1-methylpyridinium iodide in 50 ml of acetonitrile, there was added a solution of 134 mg (0.5 mmol) of 15-hydroxypentadecanoic acid and 404 mg (4.0 mmol) of triethylamine in 40 ml of acetonitrile over a period of 8 hours at a continuous and uniform rate, and the reaction mixture was refluxed for an additional 30 minutes after the addition was completed. After evaporation of the solvent, the residue was separated chromatographically on a silica gel column. 1,15-pentadecanolide was obtained in 84% yield.

EXAMPLE 2

To a refluxing solution of 510 mg (2.0 mmol) of 2-chloro-1-methylpyridinium iodide in 50 ml of acetonitrile, there was added a solution of 134 mg (0.5 mmol) of 15-hydroxypentadecanoic acid and 740 mg (4.0 mmol) of tri-n-butylamine in 40 ml of acetonitrile over a period of 8 hours at a continuous and uniform rate, and the reaction mixture was refluxed for an additional 30 minutes after the addition was completed. After evaporation of the solvent, the residue was separated chromatographically on a silica gel column. 1,15-pentadecanolide was obtained in 74% yield.

EXAMPLE 3

To a refluxing solution of 510 mg (2.0 mmol) of 2-chloro-1-methylpyridinium iodide in 50 ml of toluene, there was added a solution of 134 mg (0.5 mmol) of 15-hydroxypentadecanoic acid and 404 mg (4.0 mmol) of triethylamine in 40 ml of toluene over a period of 8 hours at a continuous and uniform rate and the reaction mixture was refluxed for and additonal 30 minutes after the addition was completed. After evaporation of the solvent, the residue was separated chromatographically on a silica gel column. 1,15 -pentadecanolide was obtained in 63%. yield.

EXAMPLE 4

To a refluxing solution of 460 mg (2.0 mmol) of 2-chloro-1-ethylpyridinium tetrafluoroborate in 50 ml of acetonitrile, there was added a solution of 134 mg (0.5 mmol) of 15-hydroxypentadecanoic acid and 404 mg (4.0 mmol) of triethylamine in 40 ml of acetonitrile over a period of 8 hours at a continuous and uniform rate, and the reaction mixture was refluxed for an additional 30 minutes after the addition was completed. After evaporation of the solvent, the residue was separated chromatographically on a silica gel column. 1,15-pentadecanolide was obtained in 75% yield.

EXAMPLE 5

To a refluxing solution of 820 mg (2.0 mmol) of 1-ethyl-2-iodoquinolinium iodide in 50 ml of acetonitrile, there was added a solution of 108 mg (0.5 mmol) of 12-hydroxydodecanoic acid and 404 mg (4.0 mmol) of triethylamine in 40 ml of acetonitrile over a period of 8.5 hours at a continuous and uniform rate, and the reaction mixture was refluxed for an additional 30 minutes after the addition was completed. After evaporation of the solvent, the residue was separated chromatographically on a silica gel column. 1,12-dodecanolide was obtained in 62% yield.

EXAMPLE 6

To a refluxing solution of 460 mg (2.0 mmol) of 2-chloro-1-ethylpyridinium tetrafluoroborate in 50 ml of dichloroethane, there was added a solution of 132 mg (1.0 mmol) of 6-hydroxyhexanoic acid and 592 mg (4.0 mmol) of 3,4-dihydro-2H-pyrido[1,2-a]pyrimidin-2-one in 40 ml of dichloroethane over a period of 7.5 hours at a continuous and uniform rate, and the reaction mixture was refluxed for an additional 30 minutes after the addition was completed. After evaporation of the solvent, the residue was separated chromatographically on a silica gel column. 1,6-hexanolide was obtained in 84% yield.

EXAMPLE 7

To a refluxing solution of 510 mg (2.0 mmol) of 2-chloro-1-methylpyridinium iodide in 50 ml of acetonitrile, there was added a solution of 150 mg (0.5 mmol) of 12-hydroxyoctadecanoic acid and 404 mg (4.0 mmol) of triethylamine in 40 ml of acetonitrile over a period of 8 hours at a continuous and uniform rate, and the reaction mixture was refluxed for an additional 30 minutes after the addition was completed. After evaporation of the solvent, the residue was separated chromatographically on a silica gel column. 12-hydroxyoctadecane-1,12-lactone was obtained in 66% yield.

EXAMPLE 8

To a refluxing solution of 486 mg (2.0 mmol) of 2-chloro-1-ethyl-3-methylpyridinium tetrafluoroborate in 50 ml of acetonitrile, there was added a solution of 129 mg ( 0.5 mmol) of 15-hydroxypentadecanoic acid and 404 mg (4.0 mmol) of triethylamine in 40 ml of acetonitrile over a period of 8 hours at a continuous and uniform rate, and the reaction mixture was refluxed for an additional 30 minutes after the addition was completed. After evaporation of the solvent, the residue was separated chromatographically on a silica gel column. 1,15-pentadecanolide was obtained in 78% yield.

What is claimed is:

1. A process for producing a lactone which comprises subjecting a hydroxy acid of the formula R—COOH wherein R is a saturated or olefinically unsaturated hydroxy acyclic group optionally substituted with cycloalkyl to intramolecular condensation by reacting said hydroxy acid with a 1-substituted-2-halopyridinium salt of the formula

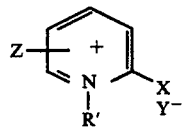

wherein R' is $C_{1-C_6}$ alkyl, allyl, $C_3$–$C_6$ cycloalkyl-($C_1$–$C_2$) alkyl, 2-oxo-($C_2$–$C_6$)alkyl, phenyl-($C_1$–$C_6$)alkyl or phenyl-substituted 2-oxo-($C_2$–$C_6$)alkyl; X is halogen; $Y^-$ is a halide ion, a methylsulfate ion, a p-toluenesulfonate ion, a perchlorate ion or a tetrafluoroborate ion; and Z is $C_1$–$C_6$ alkyl, nitro, halogen or $C_1$–$C_6$ alkoxy, or a 1-substituted-2-haloquinolinium salt of the formula

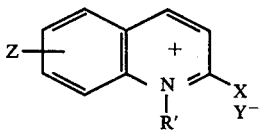

wherein R', X, Y⁻ and Z are as defined above, as a condensing agent in the presence of an acid captor for acids having an anion selected from the group consisting of halogen, methylsulfate, p-toluenesulfonate, perchlorate and tetrafluoroborate in an anhydrous organic solvent at a temperature from 0° C to the boiling point of said solvent.

2. A process according to claim 1, wherein the acid captor is a tertiary amine or a betaine selected from the group consisting of 3,4-dihydro-2H-pyrido[1,2-a]pyrimidin-2-one, triethylammonium acetate, 1-oxonianaphthalene-7-carboxylate and (1-methyl-4-pyridinio)acetate.

3. A process according to claim 1, wherein the 1-substituted-2-halopyridinium salt or the 1-substituted-2-haloquinolinium salt is selected from the group consisting of 2-chloro-1-methylpyridinium iodide, 2-iodo-1-methylpyridinium methyl sulfate, 2-chloro-1-ethylpyridinium bromide, 1-benzyl-2-chloropyridinium bromide, 2-chloro-1-phenacylpyridinium chloride, 2-fluoro-1-methylpyridinium p-toluenesulfonate, 2-bromo-1-methylpyridinium perchlorate, 1-ethyl-2-iodoquinolinium iodide, 2-chloro--ethyl-4-methoxypyridinium tetrafluoroborate and 2,6-dichloro-1-ethylpyridinium tetrafluoroborate.

4. A process according to claim 1, wherein the anhydrous organic solvent is selected from the group consisting of ethyl ether, toluene, tetrahydrofuran, benzene, xylene, acetonitrile, 1,2-dimethoxyethane, methylene dichloride, chloroform and carbon tetrachloride.

5. A process according to claim 1, wherein the acid captor is selected from the group consisting of triethylamine, tri-n-butylamine, N,N-dimethylbutylamine, N,N-dimethylcyclohexylamine, lutidine, collidine, N-methylpyrrolidine, N-methylmorpholine, 1,5-diazabicyclo[4,3,0]nonene-5, 1,4-diazabicyclo[2,2,2]octane, 1,5-diazabicyclo[5,4,0]-undecene-5, 3,4-dihydro-2H-pyrido[1,2-a]pyrimidin-2-one, triethylammonium acetate, 1-oxonianaphthalene-7-carboxylate and (1-methyl-4-pyridinio) acetate.

6. A process according to claim 1, wherein the 1-substituted-2-halopyridinium salt or the 1-substituted-2-haloquinolinium salt is used in an amount of 1 to 5 moles per mole of the hydroxy acid.

* * * * *